United States Patent [19]
Anderson

[11] Patent Number: 5,826,974
[45] Date of Patent: Oct. 27, 1998

[54] SPHERICAL ILLUMINATOR

[75] Inventor: Charles H. Anderson, Dallas, Tex.

[73] Assignee: Texas Instruments Incorporated, Dallas, Tex.

[21] Appl. No.: 688,919

[22] Filed: Jul. 31, 1996

Related U.S. Application Data

[62] Division of Ser. No. 337,588, Nov. 10, 1994, Pat. No. 5,613,753.

[51] Int. Cl.[6] ............................................. F21V 9/04
[52] U.S. Cl. ................................. 362/307; 362/299
[58] Field of Search .......................... 362/32, 300, 355, 362/356, 363, 307, 299, 350; 356/394, 236

[56] References Cited

U.S. PATENT DOCUMENTS

| | | |
|---|---|---|
| 3,427,447 | 2/1969 | Clark ........................................ 362/299 |
| 3,712,979 | 1/1973 | Padgitt . |
| 4,729,079 | 3/1988 | Maylotte . |
| 5,051,872 | 9/1991 | Anderson ................................. 362/32 |
| 5,201,576 | 4/1993 | Squyres . |

FOREIGN PATENT DOCUMENTS 58-070150  4/1983  Japan .

*Primary Examiner*—Y My Quach
*Attorney, Agent, or Firm*—Julie L. Reed; James C. Kesterson; Richard L. Donaldson

[57] ABSTRACT

A spherical illuminator (10, 40, 50, 60) having an upper diffuser (17, 47, 56, 62) with a concave surface, and having either an opposing reflector (18, 41) or an opposing lower diffuser (57, 63) with a concave surface. The two concave surfaces are placed so that their concavities form a substantially spherical viewing area into which the object under inspection is placed. The upper diffuser (10, 40, 50, 60) has a viewing aperture. It transmits light uniformly to the object from approximately two-pi steradians. The reflector (18, 41) or the lower diffuser (57, 63) provides light to the object in another two-pi steradians, resulting in nearly four-pi steradians of illumination.

3 Claims, 2 Drawing Sheets

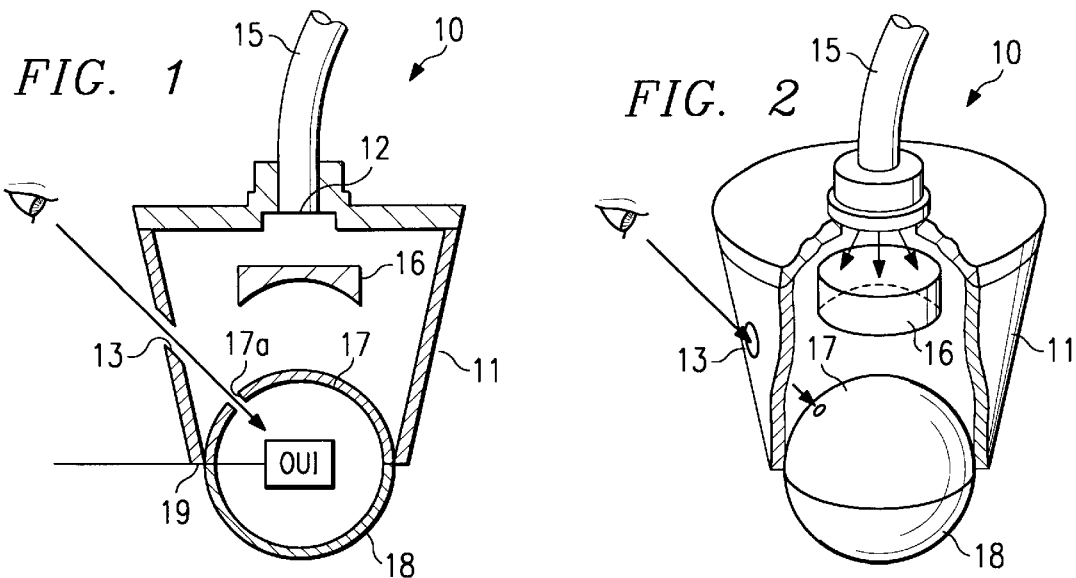
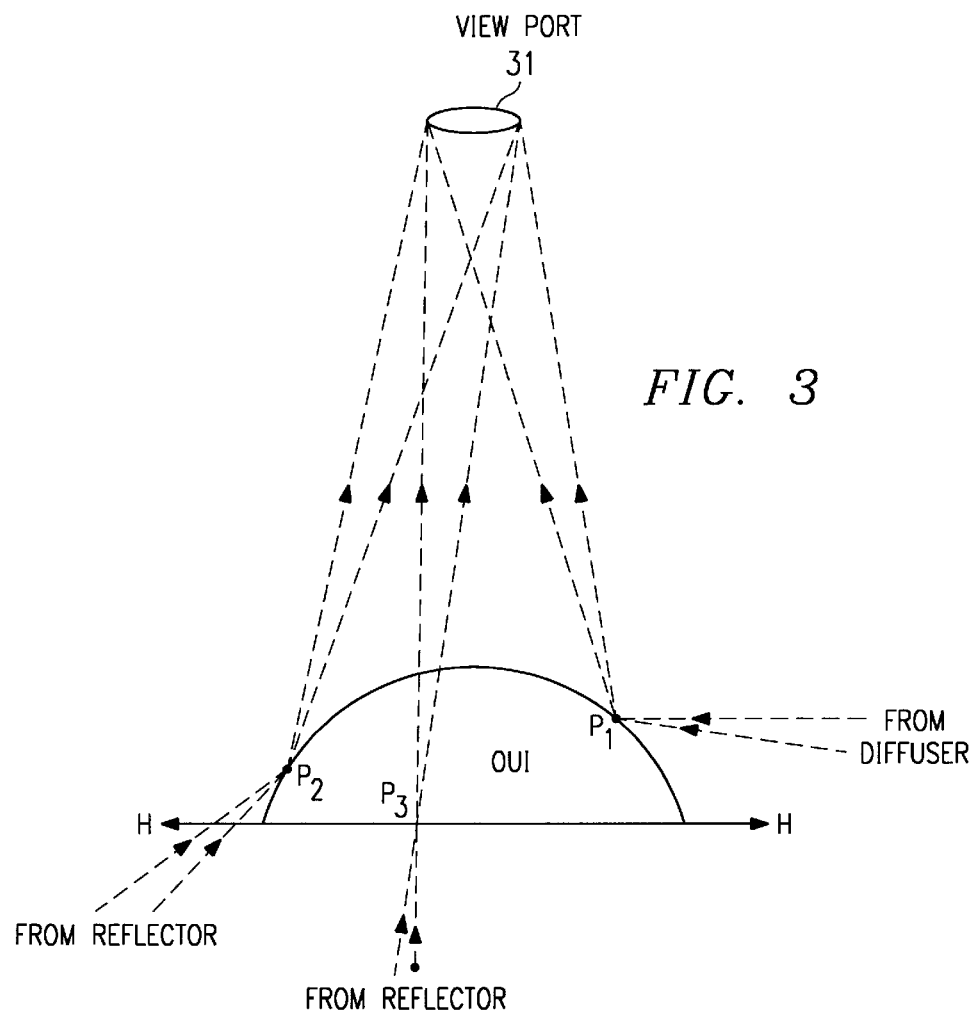

SPHERICAL ILLUMINATOR

This is a divisional, of application Ser. No. 08/337,588, filed Nov. 10, 1994, now U.S. Pat. No. 5,613,753, filed Mar. 25, 1997.

TECHNICAL FIELD OF THE INVENTION

This invention relates to optical devices, and more particularly to an illuminator for a visual inspection system.

BACKGROUND OF THE INVENTION

Visual inspection systems can be designed for use by human inspectors or for "machine vision" systems. In recent years, with the miniaturization of electrical and electromechanical devices, a particular need has arisen for inspection systems capable of detecting flaws in objects having very small features.

Most inspection systems include some sort of light source. Conventional light sources include incandescent and fluorescent lamps and light emitting diodes. Various optical arrangements have been designed for better illumination, such as ringed lamp arrays, focussed filament projectors, and fiber optic emitters. However, these conventional illuminators tend to result in "hot spots" and other viewing difficulties.

U.S. Pat. No. 5,051,872, entitled "Hemispherical Non-Glare Illuminator", assigned to Texas Instruments Incorporated, describes an illuminator that provides shadowless and uniform illumination. The illuminator has a translucent hemispherical diffuser that is placed between a light source and the object to be viewed. The concavity of the diffuser is toward the object to be viewed. The diffuser absorbs light incident on the convex surface, and emits the light diffusely from the concave surface.

SUMMARY OF THE INVENTION

One aspect of the invention is a spherical illuminator for shadowless illumination of an object under inspection. The illuminator has an upper diffuser having a substantially hemispherical surface that is concave such that it forms an inner viewing area. This upper diffuser provides transmitted illumination from substantially all of the area of its inner surface, and has an aperture for permitting the object to be viewed from outside the upper diffuser. This upper diffuser provides two-pi or nearly two-pi steradians of illumination. The illuminator also has either a reflector or a second diffuser. In either case, the reflector or second diffuser has a substantially hemispherical surface that opposes the concave surface of the upper diffuser. The reflector or second diffuser provides illumination from substantially all of the area of its inner surface, and thereby provides another two-pi steradians of illumination.

An advantage of the invention is that it provides nearly four-pi steradians of illumination. It eliminates hot spots and glare from objects that have shiny, specular, or otherwise highly reflective features. It also permits full inspection of objects that have irregular features by avoiding shadows that would otherwise be caused by such features.

BRIEF DESCRIPTION OF THE DRAWINGS

FIG. 1 is a side sectional view of an illuminator in accordance with the invention, having an off-axis view port and a remote light source.

FIG. 2 is a perspective view of the illuminator of FIG. 1.

FIG. 3 illustrates the operation of an illuminator in accordance with the invention.

DETAILED DESCRIPTION OF THE INVENTION

Figure 4:
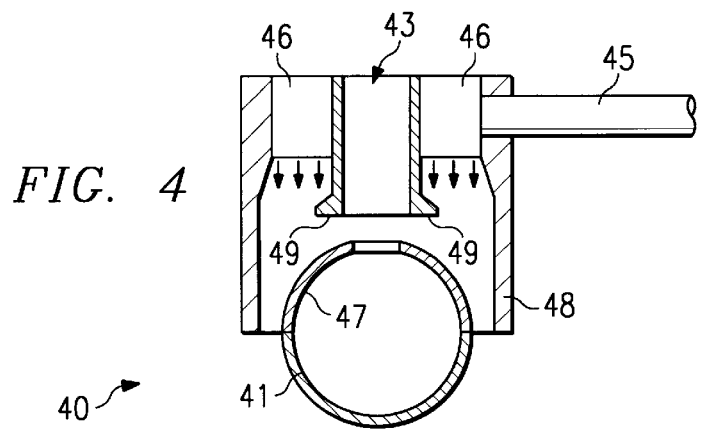
FIG. 4 is a side sectional view of an alternative embodiment of the illuminator, which has an on-axis view port and an internal light source.

FIGS. 1 and 2 are a side sectional view and a perspective view, respectively, of a spherical illuminator 10 in accordance with the invention. As explained below, illuminator 10 has a hemispherical diffuser 17 and a hemispherical reflector 18, which provide shadowless illumination from "horizon-to-horizon" of an object under inspection (OUI).

The following description emphasizes those aspects of the invention that involve reflector 18 and alternative embodiments thereof. Because of reflector 18, illuminator 10 is a "spherical" as opposed to a "hemispherical" illuminator. Details of a hemispherical illuminator are set out in U.S. Pat. No. 5,051,872, entitled "Hemispherical Non-glare Illuminator", assigned to Texas Instruments Incorporated, and incorporated by reference herein.

Illuminator 10 has a housing 11 whose inner surface is reflective, at least in part, consistent with the light path described below. Housing 11 is at least substantially light-blocking except for a light port 12 and a view port 13.

A fiber optic cable 15 provides the source illumination. Cable 15 enters illuminator 10 via light port 12. The light carried by cable 15 can be generated by various means, but is typically generated by a lamp. The radiation carried by cable 15 is not limited to visible light, and can be ultraviolet or infrared. Light cable 15 terminates at light port 12. The light rays emitted from the termination end of cable 15 diverge due to the aperture function.

Many variations for obtaining the source illumination are possible. Instead of being transmitted by a cable 15, light could be provided by a local source at port 12. Also, as explained below in connection with FIG. 5, illuminator 10 could include an internal local source, such as a fiber optic ring or an annular lamp.

The incoming light rays are incident upon a negative lens 16, which causes the rays to diverge so that they are incident on the upper surface of a convex diffuser 17, as well as on the interior wall of housing 11 which is reflective where it surrounds the lower contour of diffuser 17. The angle of the wall of housing 11 and the cavity surrounded by the housing are designed so that all of diffuser 17 is uniformly illuminated either by light rays directly from light port 12 or after reflection from the wall of housing 11.

Diffuser 17 is a hollow hemisphere. Its diffusing characteristics can be inherent in the medium of diffuser 17 or can be provided by coating or texturing either surface of diffuser 17. Examples of suitable material for diffuser 17 are milk glass, lexan, or polypropylene. The diffusive characteristic can be imparted by means such as sandblasting the surface of diffuser 17.

Diffuser 17 provides two-pi steradians of illumination, or nearly so, depending on various factors such as its diameter and the size of view port 13. Diffuser 17 is referred to herein as the "upper" diffuser, to distinguish it from additional diffusers used in other embodiments.

Reflector 18 is also a hollow hemisphere. Reflector 18 is designated as such because its concave surface is reflective.

Reflector 18 is "opposing" with respect to diffuser 17 in the sense that its concave surface is opposite the concave surface of diffuser 17 to form a spherical viewing area. In FIGS. 1 and 2, reflector 18 is approximately the same diameter as diffuser 17. However, this is not necessary, and in some cases, it may be desirable for reflector 18 to have a larger or smaller diameter.

Reflector 18 has a diffusive surface, which can be accomplished by various means. For example, the inner surface of reflector 18 could be coated with a white film or paint. Or, reflector 18 could have white plastic surface that has been sandblasted to give it a diffusive characteristic.

Reflector 18 is detachable from housing 11, to permit the OUI to be inserted into the viewing area. A holding tool may be used to support the OUI within the viewing area. This tool may extend outside housing 11 through a tool port 19. In the example of this description, the tool port 19 is at the junction where reflector 18 detaches from housing 11. The tool can be rotated, translated, or otherwise manipulated for different views of the OUI.

View port 13 in housing 11 is aligned with an aperture 17*a* in diffuser 17, so as to permit viewing of the OUI by the human eye or by devices such as a camera or a microscope. In FIGS. 1 and 2, view port 13 is offset from an optical axis that is normal to the top of the OUI when the OUI is placed in the viewing area. This configuration of view port 13 is an example of an "off-axis" configuration.

In FIGS. 1 and 2, illuminator 10 is oriented with respect to OUI, such that the diffuser 17 is the "upper" hemisphere and reflector 18 is the "lower" hemisphere. However, in other embodiments, these orientations could be reversed, such that the view port is in reflector 18 rather than in diffuser 17.

FIG. 3 illustrates the operation of a spherical illuminator in accordance with the invention. Only a view port 31 is explicitly shown. However, although not explicitly shown, the illuminator of FIG. 3 has a diffuser and reflector similar to those of FIGS. 1 and 2, as well as an aperture in the diffuser through which light may pass to view port 31. An OUI has been placed inside the illuminator, as shown in FIG. 1. In FIG. 3, the illuminator has an "on-axis" view port 31 as compared to the "off-axis" view port of FIGS. 1 and 2.

In the example of FIG. 3, the OUI is mound-shaped. Three points, P1, P2, and P3, on the OUI are illustrated. For simplicity, the eye of the viewer or the lens of the viewing device is assumed to be at the view port 31. For each point, the light that must enter the eye or lens is illustrated in dotted lines. For each point, these light rays form a "solid angle" to the lens. For this "outgoing" light to be available, that point must be illuminated with light from within a specific solid angle of incident light. For point P1, this incident light arrives after being transmitted through diffuser 17. However, for points P2 and P3, this incident light arrives after being reflected from reflector 18.

Point P2 is nearer to the horizontal line, H—H, upon which the OUI rests than is point P1. Point P3 is at the horizon. It is thus clear from FIG. 3, that illuminator provides horizon-to-horizon viewing of all points on the OUI. Expressed another way, the illuminator provides light uniformly in a solid angle of four-pi steradians (360 degrees). There are no "dark zones" from which light does not reach the eye or lens.

FIG. 4 illustrates another illuminator 40, which has a reflector 41 similar to reflector 18 of FIGS. 1 and 2. However, the view port 43 of illuminator 40 is on-axis. A fiber optics cable 45 terminates at a light ring 46, which is an annulus of light emitting fibers. Light ring 46 directs light rays to be incident on the surface of diffuser 47, whether directly or after reflection from the inner surface of housing 48 or from reflectors 49.

Figure 5:
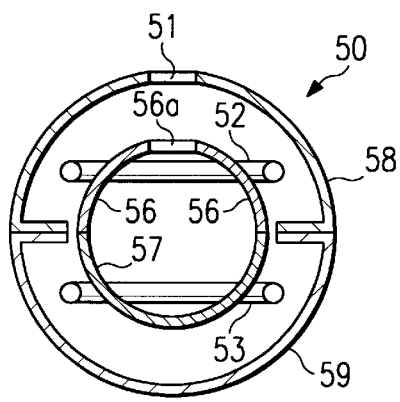
FIG. 5 is a side sectional view of an alternative embodiment of the illuminator, which has a second diffuser and light source, rather than a reflector.

FIG. 5 illustrates an alternative embodiment of the invention, referred to as an "active spherical illuminator" 50. In the embodiments of FIGS. 1 and 2 and of FIG. 4, reflectors 18 and 41 are passive in the sense that neither provides additional light. However, illuminator 50 has a lower diffuser 57 instead of a reflector. Instead of reflecting light into the viewing area after that light has been transmitted through the upper diffuser 56, lower diffuser 57 itself transmits light into the viewing area. Lower diffuser 57 is substantially the counterpart of upper diffuser 56, except that upper diffuser 56 has a viewing aperture 56*a* in line with view port 51.

In FIG. 5, the light transmitted through upper diffuser 56 and lower diffuser 57 is obtained from a local source for each. In this example, illuminator 50 has two annular lamps 52 and 53. An upper housing 58 and a lower housing 59 have reflective inner walls so that light is uniformly transmitted by the entire surface of upper diffuser 56 and lower diffuser 57.

Figure 6:
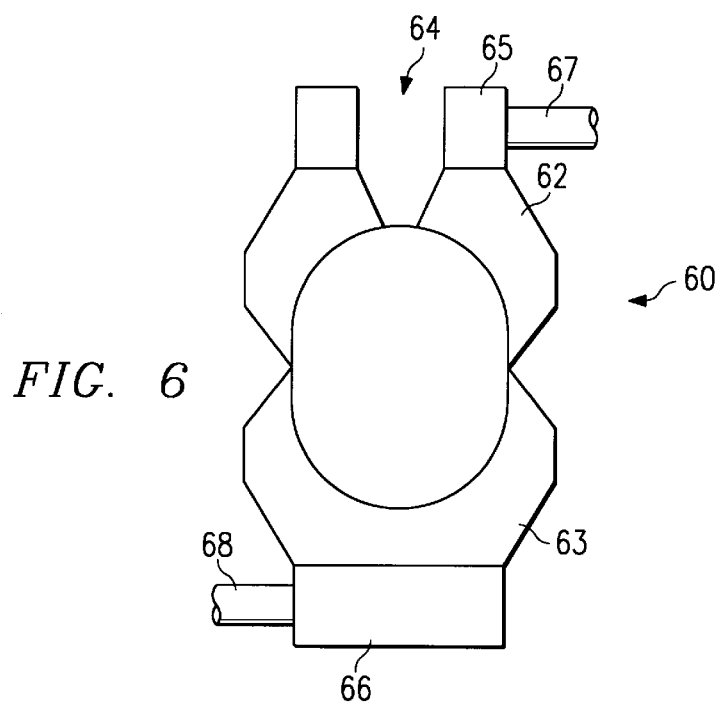
FIG. 6 is a side sectional view of an alternative embodiment of the illuminator, which has two solid diffusers.

FIG. 6 illustrates another illuminator 60, which like illuminator 50 is "active". However, instead of having diffusers that are hollow spheres, illuminator 60 has two one-piece diffusers 62 and 63. Each diffuser 62 and 63 feeds a spherical cavity 61, which acts as a diffuse light radiator. This cavity's outer surface is treated to acquire a diffusing property. Like the reflectors and diffusers of other embodiments, the conical diffusers 62 and 63 are opposing.

Diffuser 62 has a view port 64. Both diffusers 62 and 63 have an associated light ring 65 and 66, respectively, for illuminating that diffuser. Light enters the light rings 65 and 66 via fiber optic cables 67 and 68.

The inner surfaces of diffusers 62 and 63 are angled to achieve internal reflection of light from the light rings 65 and 66, and especially to direct light to the areas of the diffusers that receive little or no light directly. In this manner, the concave surfaces of diffusers 62 and 63 are uniformly illuminated.

In each of the above embodiments of the spherical illuminator, the diffuser of the upper hemisphere and the reflector or diffuser of the lower hemisphere have been described as "substantially hemispherical". As this implies, either may be flattened to provide for a more compact illuminator without departure from the basic concept of the invention.

As is evident from the above-described embodiments, for both the upper diffuser and for the lower diffuser, if there is a lower diffuser, many variations are possible with respect to the view port, light port, and light source. For example, the light ring 53 configuration of FIG. 5 could be used with an "off-axis" view port. Also, an "on-axis" view port could be used with an "off-axis" fiber optic cable. Another alternative is a local light source in the form of one or more annular lamps or a spiral neon lamp above the diffuser. Also, a beam splitter could be placed over the aperture in the diffuser so as to avoid a dark spot. Further details about these variations are set out in U.S. Pat. No. 5,051,872, referenced above.

OTHER EMBODIMENTS

Although the invention has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the invention.

What is claimed is:

1. A spherical illuminator for shadowless illumination of an object under inspection, comprising:

a diffuser having a substantially hemispherical, concave surface such that it forms an inner viewer area, said diffuser providing transmitted illumination from a light source mounted outside of said diffuser, wherein said diffuser transmits light from substantially all of the area of its inner surface;

a reflector having a substantially hemispherical surface that is concave and that opposes the concave inner surface of said diffuser, forming a cavity said reflector providing reflected illumination from substantially all of its inner surface;

wherein one of said diffuser for said reflector has an aperture for permitting said object in said cavity to be viewed.

2. The illuminator of claim 1, said light source further comprising a fiber optic ring for providing light to be transmitted through said diffuser.

3. The illuminator of claim 1, said light source further comprising an annular lamp for providing light to be transmitted through said diffuser.

* * * * *